United States Patent [19]

Yoshihara et al.

[11] Patent Number: 5,332,581
[45] Date of Patent: Jul. 26, 1994

[54] KERATINOUS FIBER TREATING COMPOSITION

[75] Inventors: Toru Yoshihara; Takayoshi Kajino; Emi Chugun, all of Tokyo, Japan

[73] Assignee: Kao Corporation, Tokyo, Japan

[21] Appl. No.: 936,630

[22] Filed: Aug. 28, 1992

[30] Foreign Application Priority Data

Aug. 30, 1991 [JP] Japan ............... 3-219952

[51] Int. Cl.$^5$ .......................... A61K 7/075
[52] U.S. Cl. .......................... 424/70; 424/71; 424/401; 514/717; 514/718; 514/881; 8/429
[58] Field of Search .................... 424/70, 71

[56] References Cited

U.S. PATENT DOCUMENTS

| | | | |
|---|---|---|---|
| 3,650,280 | 3/1972 | Roberts et al. | 132/7 |
| 4,221,729 | 9/1980 | Kalopissis et al. | 260/396 N |
| 4,337,061 | 6/1982 | Bugaut et al. | 8/405 |
| 4,370,142 | 1/1983 | Bugaut et al. | 8/407 |
| 4,555,247 | 11/1985 | de la Mettrie et al. | 8/405 |

FOREIGN PATENT DOCUMENTS

0406887 10/1991 European Pat. Off. .

OTHER PUBLICATIONS

Database WPIL, Class D25, AN 88-124391, & JP-A-63 069 897, Mar. 29, 1988, "Detergent Composition For Heavy Dirt Attached to Hard Surfaces-Comprise Amine, High B.PT. Solvent and Surfactant".

*Primary Examiner*—Thurman K. Page
*Assistant Examiner*—Jyothsna Venkat
*Attorney, Agent, or Firm*—Oblon, Spivak, McClelland, Maier & Neustadt

[57] ABSTRACT

A keratinous fiber treating composition comprising the following components (a) and (b), and an acid.

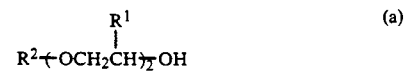

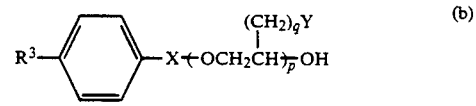

The keratinous fiber treating composition according to the present invention makes it possible to impart a good elasticity to the hair without causing any damage (for example, dryness, stiffness and splitting) thereof.

4 Claims, No Drawings

KERATINOUS FIBER TREATING COMPOSITION

FIELD OF THE INVENTION

This invention relates to a keratinous fiber treating composition which can impart a good elasticity to keratinous fibers (such as hair) and exert excellent effects of preventing damages (for example, dryness, stiffness, splitting, etc.) thereon.

BACKGROUND OF THE INVENTION

A known method for imparting an elasticity to the hair comprises, for example, using a hair cosmetic containing a polymeric substance to be adsorbed on the surface of the hair. As a hair cosmetic of this type, a hair rinse, which is applied to the hair and then washed away is examplified.

However, a hair cosmetic of this type is disadvantageous in that the polymeric substance is adsorbed on the hair surface only in an insufficient amount, and as a result, the desired effects cannot be fully achieved. In addition, it causes damages (for example, dryness, stiffness, etc.) of the hair and deteriorates the texture thereof.

On the other hand, it has been known to impart an elasticity to the hair by astringing the hair with the use of a hair cosmetic containing an astringent.

In this case, however, the hair is seriously damaged (stiff and dry) and the hair texture is deteriorated, similar to the above-mentioned method.

SUMMARY OF THE INVENTION

It is an object of the present invention to provide a novel keratinous fiber treating composition which can impart a good elasticity to keratinous fibers (such as the hair) without damaging the same.

As a result of the extensive investigations to solve the above-mentioned problems, the present inventors successfully found that a composition, wherein a specific dialkylene glycol monoalkyl ether is combined with a specific aromatic alcohol derivative and an acid, can impart an elasticity to keratinous fibers such as the hair, prevent the hair from damages due to swelling during shampooing, and exert conditioning (moisturizing) effects thereon after drying without causing dryness and stiffness, thus completing the present invention.

Accordingly, the present invention provides a keratinous fiber treating composition comprising the following components (a), (b) and (c):

(a) a dialkylene glycol monoalkyl ether represented by formula (1):

wherein $R^1$ represents a hydrogen atom, or a methyl group; and $R^2$ represents an alkyl group having from 1 to 5 carbon atoms;

(b) an aromatic alcohol represented by formula (2):

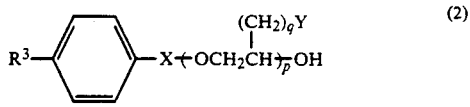

wherein $R^3$ represents a hydrogen atom, a methyl group, or a methoxy group; X represents a single bond, a straight-chain or branched-chain alkylene group having from 1 to 3 carbon atoms, or a straight-chain or branched-chain alkenylene group having from 1 to 3 carbon atoms; Y represents a hydrogen atom, or a hydroxyl group; and p and q each represent 0 or an integer of from 1 to 5; and (c) an acid.

DETAILED DESCRIPTION OF THE INVENTION

The component (a) to be used in the present invention is a dialkylene glycol monoalkyl ether represented by the above general formula (1). Specific examples thereof include diethylene glycol monomethyl ether, diethylene glycol monoethyl ether, diethylene glycol monopropyl ether, diethylene glycol monobutyl ether, diethylene glycol monopentyl ether, diethylene glycol monoisopropyl ether, diethylene glycol mono-t-butyl ether, dipropylene glycol monomethyl ether, dipropylene glycol monoethyl ether, dipropylene glycol monopropyl ether, dipropylene glycol monobutyl ether, dipropylene glycol monopentyl ether, dipropylene glycol monoisopropyl ether and dipropylene glycol mono-t-butyl ether. Among these dialkylene glycol monoalkyl ethers, diethylene glycol monoethyl ether, diethylene glycol monopropyl ether and diethylene glycol monobutyl ether are particularly preferred.

The content of the component (a) in the keratinous fiber treating composition of the present invention is not particularly restricted. A common preparation may contain from 1 to 90% (by weight, the same will apply hereinafter), preferably from 1 to 50% and more preferably from 2 to 20% of the component (a). Its content less than 1% is undesirable, since the effects of the present invention cannot be fully achieved in this case.

The component (b) to be used in the present invention is an aromatic alcohol represented by the above general formula (2). Specific examples thereof include benzyl alcohol, cinnamyl alcohol, phenethyl alcohol, p-anisyl alcohol, p-methylbenzyl alcohol, phenoxyethanol and 2-benzyloxyethanol.

The component (b) contributes to the uniform dissolution of the components (a) and (c) so as to promote the penetration of these components into keratinous fibers. Thus, the content of the component (b) in the composition of the present invention preferably ranges from 0.5 to 50%, more preferably from 2 to 30%. When the content of this component (b) is less than 0.5%, the above-mentioned effects cannot be fully achieved. On the other hand, its content exceeding 50% is not preferable, since the effects cannot be improved any more in this case.

It is preferable to use a weak acid as the acid used as the component (c), since the hair per se has an ion-exchange action. Specific examples of the weak acid include citric acid, glycolic acid, succinic acid, tartaric acid, lactic acid, acetic acid, fumaric acid, malic acid, levulinic acid, butyric acid, valeric acid, oxalic acid, maleic acid, mandelic acid and phosphoric acid. It is further preferable to convert a part of these weak acids to, for example, its potassium, sodium, ammonium or alkanolamine salt so as to impart a buffer action to the system. The content of these acids in the composition of the present invention may preferably range from 0.01 to 25%, more preferably from 0.1 to 15%.

It is preferable to control the pH value of the whole composition within a range of 2 to 5 with the use of, for example, the above-mentioned acids and the salts.

The keratinous fiber treating composition of the present invention may further contain a conventional lower ($C_1$ to $C_4$) alcohol or a lower ($C_1$ to $C_4$) polyol in order to elevate the solubility of the aromatic alcohol derivative of the component (b) in the composition. More particularly, ethanol, isopropanol, n-propanol, n-butanol, isobutanol, ethylene glycol, propylene glycol, 1,3-butanediol or glycerol may be used therefor.

It is preferable that the keratinous fiber treating composition of the present invention is formulated into a hair dye composition containing known direct dyes in order to elevate the elasticity of keratinous fibers and to change the color tone thereof. These direct dyes would deeply penetrate into the hair, similar to the abovementioned components (a) and (c).

Examples of these direct dyes include dyes of nitro-series such as 3-amino-4-hydroxynitrobenzene, 2-amino-5-hydroxynitrobenzene, 2-amino-3-hydroxynitrobenzene, 2-amino-5N,N-bis-β-hydroxyethylaminonitrobenzene, 2-amino-4-chloro-5-N-β-hydroxyethylaminonitrobenzene, 2-amino-4-methyl-5-N-β-hydroxyethylaminonitrobenzene, 3,4-bis-(N,β-hydroxyethylamino)nitrobenzene, 2-amino-4-methyl-5-N-β,γ-dihydroxypropylaminonitrobenzene, 2-amino-4-methyl-5-β-aminoethylamino-nitrobenzene and 2-amino-4-hydroxynitrobenzene; and, as still more prefer examples, 3,4-diaminonitrobenzene, 2,5-diaminonitrobenzene, 2-amino-5-β-N-hydroxyethylaminoitrobenzene, 2-N-β-hydroxyethylamino-5-N,N-bis-β-hydroxyethylaminonitrobenzene, 2-N-methylamino-5-N,N-bis(β-hydroxyethyl)aminonitrobenzene, 2-N-methylamino-5-N-methyl-N-β-hydroxyethylaminonitrobenzene, 2-N-β-hydroxyethylamino-5-hydroxynitrobenzene, 3-methoxy-4-N-β-hydroxyethylaminonitrobenzene, 4-nitro-3-methylaminophenoxyethanol, 2-N-β-hydroxyethylamino-5-aminonitrobenzene, 2-N-β-hydroxyethylaminonitrobenzene, 3-amino-4-N-β-hydroxyethylaminonitrobenzene, 3-β-hydroxyethyloxy-4-N-β-hydroxyethylaminonitrobenzene, 2-amino-5-N-methylaminonitrobenzene, 2-amino-3-methylnitrobenzene, 2,5-diaminonitrobenzene, 2-N-β-hydroxyethylamino-5-β,γ-dihydroxypropyloxyn 3-hydroxy-4-N-β-hydroxyethylaminonitrobenzene; 3-hydroxy-4-aminonitrobenzene, 2,5-N,N'-β-hydroxyethylaminonitrobenzene, 2-N-methylamino-4-o-β,γ-dihydroxypropyloxynitrobenzene, 2-N-β-aminoethylamino-5-N,N'-bis-(β-hydroxyethyl)aminonitrobenzene, 2-N-β-aminoethylamino-4-methoxynitrobenzene, and 2-N-β-aminoethylamino-5-β-hydroxyethyloxynitrobenzene; anthraquinone-direct dyes such as 1-amino-4-methylaminoanthraquinone and 1,4-diaminoanthraquinone; acid dyes such as Acid Red 27, Acid Red 51, Acid Red 18, Acid Red 92, Acid Red 94, Acid Red 52, Acid Yellow 23, Food Yellow 3, Food Green 3, Food Blue 2, Acid Blue 74, Acid Red 33, Acid Red 87, Acid Red 92, Acid Red 94, Acid Orange 7, Acid Red 95, Acid Yellow 73, Acid Yellow 3, Acid Green 25, Solvent Green 7, Acid Green 5, Acid Blue 5, Acid Blue 9, Acid Orange 24, Acid Violet 9, Food Red 6, Acid Red 26, Food Red 1, Acid Red 88, Acid Orange 20, Acid Yellow 40, Acid Yellow 1, Acid Yellow 36, Acid Yellow 11, Acid Green 1, Acid Green 3, Acid Violet 43 and Acid Black 1; disperse dyes such as Solvent Red 49, Solvent Red 48, Solvent Red 23, Solvent Red 72, Solvent Red 73, Acid Yellow 73, Solvent Yellow 33, Solvent Green 3, Solvent Violet 13, Solvent Red 24, Solvent Orange 7, Solvent Orange 2, Solvent Yellow 5, Solvent Yellow 6, Solvent Blue 63 and Solvent Red 43; basic dyes such as Basic Violet 10 and Solvent Red 49; and basic dyes manufactured by Williams Co. such as Sienna Brown, Mahogany, Madder Red, Steel Blue and Straw Yellow.

Although the content of these direct dyes may vary depending on the desired elasticity and color tone of the keratinous fibers, it preferably ranges from 0.08 to 5%, more preferably from 0.15 to 3%, based on the total composition according to the present invention.

In addition to the above-mentioned components, the keratinous fiber treating composition of the present invention may further contain appropriate components commonly employed in the field of cosmetics.

The keratinous fiber treating composition of the present invention may contain one or more surfactants selected, for example, from anionic surfactants such as alkylbenzenesulfonates, alkyl ether sulfates, olefinsulfonates, α-sulfo fatty acid esters, amino acid type surfactants, phosphate type surfactants and sulfosuccincate type surfactants; cationic surfactants such as quaternary ammonium salts having straight-chain and/or branched alkyl groups as described, for example, in U.S. Pat. Nos. 4,711,776 and 4,910,013; amphoteric surfactants such as sulfonic acid-type surfactants, betaine-type surfactants, alkylamine oxides and imidazoline-type surfactants; and nonionic surfactants such as polyoxyethylene alkyl ethers, polyoxyethylene alkylphenyl ethers, alkanol amides and alkylene oxide adducts thereof, esters of polyhydric alcohols with fatty acids, sorbitan fatty acid esters and alkyl saccharide-type surfactants. The keratinous fiber treating composition according to the present invention preferably contains these surfactants in an amount of from 0.01 to 40.0%, more preferably from 0.05 to 20.0%, based on the total weight of the composition.

Further, the keratinous fiber treating composition of the present invention may contain one or more cationic polymers selected, for example, from cationized cellulose derivatives, cationic starch, cationized guar gum derivatives, diallyl quaternary ammonium salt/acrylamide copolymers and quaternized polyvinylpyrrolidone derivatives so as to improve the texture of the hair. Preferred examples of these cationic polymers include cationized cellulose of an average molecular weight ranging from approximately 100,000 to 3,000,000, cationic starch of a degree of cationization ranging from approximately 0.01 to 1, cationized guar gum of a degree of cationization of from approximately 0.01 to 1 (for example, Jaguar manufactured by Meyhall Chemical AG), diallyl quaternary ammonium salt/acrylamide copolymers of an average molecular weight ranging from approximately 30,000 to 2,000,000, quaternized polyvinylpyrrolidone derivatives of an average molecular weight ranging from approximately 10,000 to 2,000,000 and a cationic nitrogen content in the vinyl polymer ranging from 0.004 to 0.2%, and cationic polymers described in U.S. Pat. Nos. 5,009,880 and 4,597,962. The keratinous fiber treating composition according to the present invention may preferably contain these cationic polymers in an amount of from 0.05 to 20.0%, more preferably from 0.1 to 10.0%.

Furthermore, the keratinous fiber treating composition of the present invention may contain one or more silicone derivatives selected, for example, from dimethyl-polysiloxane, methylphenylpolysiloxane, amino-modified silicone, fatty acid-modified silicone, alcohol-modified silicone, aliphatic alcohol-modified silicone, polyether-modified silicone, epoxy-modified silicone, fluorine-modified silicone, cyclic silicone and alkyl-modified silicone so as to improve the texture of the hair or the skin.

These silicone derivatives may be used either in the form of a single compound or in the from of a latex composition thereof obtained through emulsion-polymerization by the method described, for example, in U.S. Pat. No. 4,228,054 may be used in the present invention. Among these silicone derivatives, dimethylpolysiloxane (degree of polymerization: 500 or above), polyether-modified silicone, amino-modified silicone and cyclic silicone are particularly preferable since they impart a good texture to the hair. The keratinous fiber treating composition of the present invention may preferably contain these silicone derivatives in an amount of from 0.01 to 20.0%, more preferably from 0.05 to 10.0%, based on the total weight of the composition.

In addition, the keratinous fiber treating composition of the present invention may further contain, if desired, components commonly employed in the fields of cosmetics, for example, texture improvers such as higher fatty acid salts, alkylamine oxides, fatty acid alkanol amides, squalene and lanolin; humectants such as sorbitol and amide derivatives represented by formula (3):

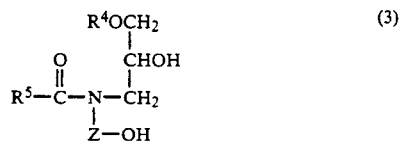

wherein $R^4$ represents a straight-chain or branched-chain, saturated or unsaturated hydrocarbon group having from 10 to 26 carbon atoms, preferably 12 to 20 carbon atoms; $R^5$ represents a straight-chain or branched, saturated or unsaturated hydrocarbon group having from 9 to 25 carbon atoms, preferably 12 to 20 carbon atoms; and Z represents $-(CH_2)_m-$ wherein m is an integer of 2 to 6; thickening agent such as methylcellulose, carboxyvinyl polymer, hydroxyethylcellulose and polyoxyethyleneglycol distearate; pearling agents; perfumes; UV absorbers; antioxidants; bactericides such as trichlorocarbanilide; anti-inflammatory agents such as dipotassium glycyrrhizinate and tocopherol acetate; anti-dandruff agents such as zinc pyrithione and octopifox; and preservatives such as methylparaben and butylparaben, so long as the effects of the present invention are not deteriorated thereby.

When the keratinous fiber treating composition of the present invention is applied to keratinous fibers, it is desirable that the keratinous fiber treating composition of the present invention is applied to the hair, heated at 30° to 50° C. for 10 to 35 minutes, and then washed away to thereby achieve further improved effects.

The application of the keratinous fiber treating composition according to the present invention makes it possible to impart a good elasticity to keratinous fibers such as the hair without causing any damage (for example, dryness, stiffness and splitting) of the keratinous fibers such as the hair.

The present invention is further illustrated in greater detail by the following examples, but the present invention is not limited thereto.

EXAMPLES 1 TO 7 AND COMPARATIVE EXAMPLES 1 AND 2

Keratinous fiber treating compositions as listed in Table 1 were prepared and the performance of each product was evaluated by the following method. The results are shown in Table 1. Evaluation method:

About 20 g (length: 15-20 cm) of the hair of a Japanese female subject, which had never been cold-permed or bleached, was bundled and shampooed. Then, 10 g of a keratinous fiber treating composition was uniformly applied to this hair, followed by heating at 45° C. for 20 minutes. After rinsing with running water, the hair was towel-dried and further treated with a dryer. The softness, oily feel, smoothness, elasticity and splitting of the treated hair were evaluated based on the following criteria.

(1) Softness
  ⊚: Very soft.
  ○: Soft.
  Δ: Uncertain.
  x: Hard.
(2) Oily feel
  ⊚: Scarcely oily.
  ○: Less oily.
  Δ: Uncertain.
  x: Seriously oily.
(3) Smoothness
  ⊚: Very smooth.
  ○: Smooth.
  Δ: Uncertain.
  x: Not smooth.
(4) Elasticity
  ⊚: Very elastic.
  ○: Elastic.
  Δ: Uncertain.
  x: Not elastic.
(5) Splitting
A hair bundle treated in the same manner as the one described above was brushed definite times, and then the splitting was evaluated in accordance with the following criteria, compared with the hair bundle prior to brushing.
  ⊚: Not worsened.
  ○: Scarcely worsened.
  Δ: Somewhat worsened.
  x: Serious splitting.

TABLE 1

| | Example | | | | | | | Comparative Example | |
|---|---|---|---|---|---|---|---|---|---|
| | 1 | 2 | 3 | 4 | 5 | 6 | 7 | 1 | 2 |
| Component (wt %) | | | | | | | | | |
| hydroxyethylcellulose | 1.6 | 1.6 | 1.6 | 1.6 | 1.6 | 1.6 | 1.6 | 1.6 | 1.6 |
| benzyl alcohol | 6.0 | — | — | 6.0 | 6.0 | 6.0 | 6.0 | 6.0 | — |
| 2-benzyloxyethanol | — | 6.0 | — | — | — | — | — | — | — |
| phenoxyethanol | — | — | 6.0 | — | — | — | — | — | — |
| ethanol | 15.0 | 15.0 | 15.0 | 15.0 | 15.0 | 15.0 | 15.0 | 15.0 | 15.0 |
| diethylene glycol | 10.0 | 10.0 | 10.0 | 10.0 | 10.0 | — | — | — | 10.0 |

TABLE 1-continued

|  | Example | | | | | | | Comparative Example | |
|---|---|---|---|---|---|---|---|---|---|
|  | 1 | 2 | 3 | 4 | 5 | 6 | 7 | 1 | 2 |
| monoethyl ether |  |  |  |  |  |  |  |  |  |
| diethylene glycol monopropyl ether | — | — | — | — | — | 10.0 | — | — | — |
| diethylene glycol monobutyl ether | — | — | — | — | — | — | 10.0 | — | — |
| cationized cellulose[1] | 0.3 | 0.3 | 0.3 | 0.3 | 0.3 | 0.3 | 0.3 | 0.3 | 0.3 |
| N-lauramide propyl betaine[2] | — | — | — | 0.3[3] | 0.3[3] | 0.3[3] | 0.3[3] | — | — |
| sodium lactate | 1.0 | 1.0 | 1.0 | 1.0 | 1.0 | 1.0 | 1.0 | 1.0 | 1.0 |
| lactic acid | 8.0 | 8.0 | 8.0 | 8.0 | 8.0 | 8.0 | 8.0 | 8.0 | 8.0 |
| Black No. 401 | — | — | — | — | 0.2 | 0.2 | 0.2 | — | — |
| purified water | balance | balance | balance | balance | balance | balance | balance | balance | balance |
| pH | 3.6 | 3.6 | 3.6 | 3.6 | 3.6 | 3.6 | 3.6 | 3.6 | 3.6 |
| Evaluation |  |  |  |  |  |  |  |  |  |
| Softness | ○ | ○ | ○ | ○ | ○ | ○ | ○ | △ | △ |
| Oily feel | ○ | ○ | ○ | ○ | ○ | ○ | ○ | △ | △ |
| Smoothness | ○ | ○ | ○ | ⊙ | ⊙ | ⊙ | ⊙ | x | △ |
| Elasticity | ○ | ○ | ○ | ○ | ⊙ | ⊙ | ⊙ | x | △ |
| Splitting | ○ | ○ | ○ | ○ | ○ | ○ | ○ | x | △ |

[1]Polymer JR-400 (Quaternium 19), manufactured by Union Carbide Co.
[2]Softazoline LPB (N-lauroylamidopropyl bentaine), manufactured by Kawaken Fine Chemicals Co.
[3]As a concentration of the active compound While the invention has been described in detail and with reference to specific embodiments thereof, it will be apparent to one skilled in the art that various changes and modifications can be made therein without departing from the spirit and scope thereof.

What is claimed is:

1. A keratinous fiber treating composition comprising the following components (a), (b) and (c):

(a) 2 to 20% by weight based on the total weight of said composition of a dialkylene glycol monoalkyl ether represented by formula (I):

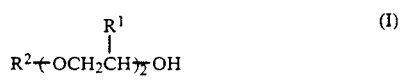

wherein $R^1$ represents a hydrogen atom, or a methyl group; and $R^2$ represents an alkyl group having from 1 to 5 carbon atoms;

(b) 2 to 20% by weight based on the total weight of said composition of an aromatic alcohol represented by formula (II):

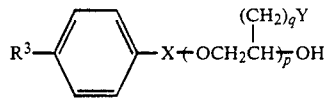

wherein $R^3$ represents a hydrogen atom, a methyl group, or a methoxy group; X represents a single bond, a straight-chain or branched-chain alkylene group having from 1 to 3 carbon atoms, or a straight-chain or branched-chain alkenylene group having from 1 to 3 carbon atoms; Y represents a hydrogen atom, or a hydroxyl group; and p and q each represents 0 or an integer of from 1 to 5; and (c) 2 to 8% by weight based on the total weight of said composition of a weak acid.

2. The keratinous fiber treating composition as claimed in claim 1, wherein the pH value is controlled within a range of 2 to 5.

3. The keratinous fiber treating composition as claimed in claim 1 further comprising a $C_1$-$C_4$ alcohol or a $C_1$-$C_4$ polyol.

4. The keratinous fiber treating composition according to claim 1, wherein said weak acid is selected from the group consisting of citric acid, glycolic acid, succinic acid, tartaric acid, lactic acid, acetic acid, fumaric acid, malic acid, levulinic acid, butyric acid, valeric acid, oxalic acid, maleic acid, mandelic acid, phosphoric acid, and salts thereof.

* * * * *